US012029497B2

(12) United States Patent
DeBuys et al.

(10) Patent No.: US 12,029,497 B2
(45) Date of Patent: Jul. 9, 2024

(54) INTERLOCKING GEAR SYSTEM FOR STERILE ROBOTIC CATHETER NAVIGATION SYSTEMS

(71) Applicant: SIEMENS HEALTHINEERS AG, Forchheim (DE)

(72) Inventors: Christian DeBuys, College Station, TX (US); Young-Ho Kim, West Windsor, NJ (US); Ankur Kapoor, Plainsboro, NJ (US); Tommaso Mansi, Plainsboro, NJ (US)

(73) Assignee: Siemens Healthineers AG, Forchheim (DE)

( * ) Notice: Subject to any disclaimer, the term of this patent is extended or adjusted under 35 U.S.C. 154(b) by 279 days.

(21) Appl. No.: 16/949,760

(22) Filed: Nov. 13, 2020

(65) Prior Publication Data

US 2021/0145522 A1 May 20, 2021

Related U.S. Application Data

(60) Provisional application No. 62/935,821, filed on Nov. 15, 2019, provisional application No. 62/935,811, filed on Nov. 15, 2019.

(51) Int. Cl.
*A61B 34/20* (2016.01)
*A61B 34/30* (2016.01)
*A61M 25/01* (2006.01)

(52) U.S. Cl.
CPC .............. *A61B 34/20* (2016.02); *A61B 34/30* (2016.02); *A61M 25/0113* (2013.01); *A61M 25/0136* (2013.01); *A61B 2034/301* (2016.02)

(58) Field of Classification Search
CPC ... A61B 34/20; A61B 34/30; A61B 2034/301; A61B 8/0883; A61B 8/12; A61B 8/445; A61B 46/10; A61B 2017/00477; A61B 2090/3784; A61M 25/0113; A61M 25/0136
USPC ........................................................ 606/130
See application file for complete search history.

(56) References Cited

U.S. PATENT DOCUMENTS

| 5,417,210 A | 5/1995 | Funda et al. |
| 7,666,191 B2 | 2/2010 | Orban et al. |
| 7,699,855 B2 | 4/2010 | Anderson et al. |
| 7,886,743 B2 | 2/2011 | Cooper et al. |

(Continued)

FOREIGN PATENT DOCUMENTS

| EP | 1906858 A1 | 4/2008 |
| WO | 2019183141 A1 | 9/2019 |

OTHER PUBLICATIONS

U.S. Appl. No. 16/907,675, filed Jun. 22, 2020, entitled "Dual Manipulation for Robotic Catheter Systems," not yet published.

(Continued)

*Primary Examiner* — Wade Miles

(57) ABSTRACT

A robotic catheter navigation system, and a method for operating the robotic catheter navigation system, are provided. The robotic catheter navigation system comprises a catheter handle, a motor, and a torque transfer disk. The catheter handle comprises a set of gears coupled to a first shaft. The motor is for rotating a second shaft. The torque transfer disk is coupled to the first shaft and the second shaft for transferring the rotation of the second shaft to the first shaft to thereby rotate the set of gears for steering a catheter.

14 Claims, 11 Drawing Sheets

(56) References Cited

U.S. PATENT DOCUMENTS

| | | |
|---|---|---|
| 8,206,406 B2 | 6/2012 | Orban et al. |
| 8,220,468 B2 | 7/2012 | Cooper et al. |
| 8,998,799 B2 | 4/2015 | Orban et al. |
| 8,998,930 B2 | 4/2015 | Orban et al. |
| 2005/0020911 A1 | 1/2005 | Viswanathan et al. |
| 2007/0296825 A1 | 12/2007 | Ito et al. |
| 2016/0361129 A1 | 12/2016 | Morrissette et al. |
| 2016/0367328 A1 | 12/2016 | Dachs et al. |
| 2018/0177561 A1 | 6/2018 | Mintz et al. |
| 2019/0038282 A1* | 2/2019 | Shelton, IV ..... A61B 17/07207 |
| 2020/0060646 A1 | 2/2020 | Lindenroth et al. |
| 2020/0061339 A1 | 2/2020 | Lindenroth et al. |
| 2020/0237453 A1* | 7/2020 | Anglese ................. A61B 90/03 |
| 2020/0261167 A1* | 8/2020 | Anglese ................. A61B 34/71 |

OTHER PUBLICATIONS

U.S. Appl. No. 16/809,067, filed Mar. 4, 2020, entitled "Mechanically-Decoupled Actuation for Robotic Catheter System," not yet published.

Loschak et al., "Predictive Filtering in Motion Compensation with Steerable Cardiac Catheters," 2017, IEEE International Conference on Robotics and Automation (ICRA), 8 pgs.

Kim et al., "Towards Automatic Manipulation of Intra-cardiac Echocardiography Catheter," 2020, IEEE Transaction on Medical Robotics and Bionics, 12 pgs.

Loschak et al., Algorithms for Automatically Pointing Ultrasound Imaging Catheters, 2016, IEEE Transactions on Robotics, 11 pgs.

Stereotaxis, "Stereotaxs V-Drive Robotic Navigation System," 2020, retrieved online from http://www.stereotaxis.com/products/#!/vdrive, 6 pgs.

U.S. Appl. No. 17/033,297, filed Sep. 25, 2020, entitled "Holder Facility for Holding a Medical Instrument" not yet published.

* cited by examiner

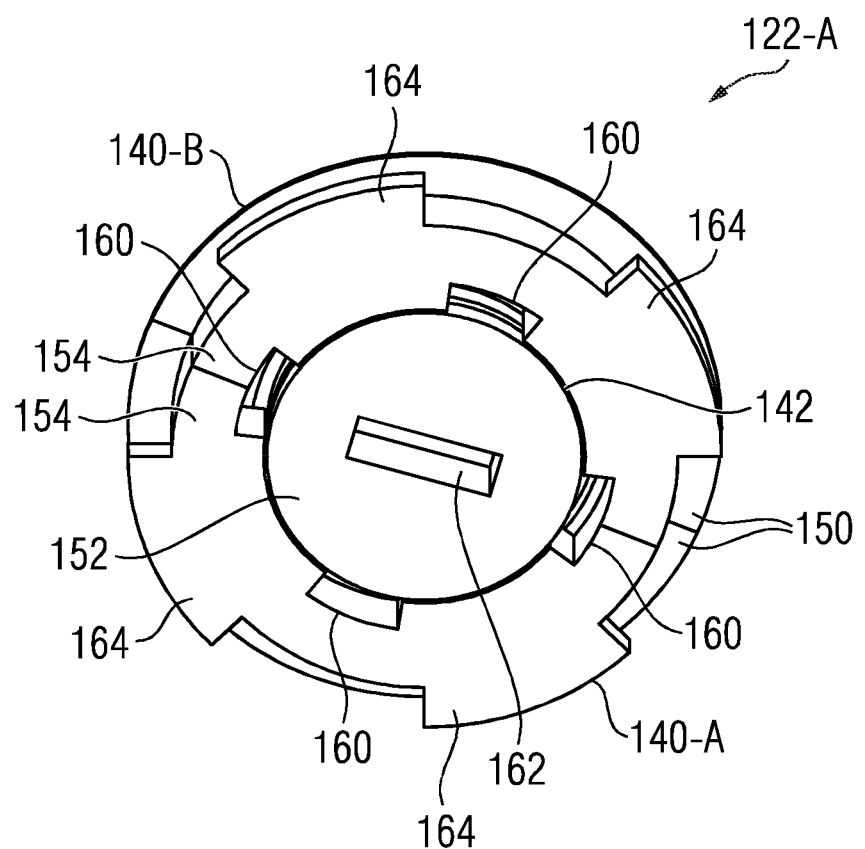

INTERLOCKING GEAR SYSTEM FOR STERILE ROBOTIC CATHETER NAVIGATION SYSTEMS

CROSS-REFERENCE TO RELATED APPLICATIONS

This application claims the benefit of U.S. Provisional Application No. 62/935,821, filed Nov. 15, 2019, and U.S. Provisional Application No. 62/935,811, filed Nov. 15, 2019, the disclosures of which are incorporated herein by reference in their entirety.

TECHNICAL FIELD

The present invention relates generally to robotic catheter navigation systems, and in particular to an interlocking gear system for sterile robotic catheter navigation systems.

BACKGROUND

ICE (intracardiac echocardiogram) is an increasingly popular imaging modality capable of generating high-resolution real-time images of cardiac structures of a patient. ICE has become an important part of cardiac electrophysiology, structural heart interventions, and other interventional cardiac procedures. Compared to transthoracic echocardiograms (TTE), transesophageal echocardiography (TEE), and other common cardiac ultrasound imaging techniques, ICE generates higher quality images, does not require that the patient undergo general anesthesia, and enables direct navigation of ICE catheters by cardiologists.

Recently, robotic catheter navigation systems have been utilized for steering ICE catheters during an ICE procedure. Such robotic catheter navigation systems comprise a catheter handle and one or more motors directly driving gears in the catheter handle for steering the catheter. One challenge associated with robotic catheter navigation systems is sterilization. Due to exposure to blood and other contaminants, robotic catheter navigation systems are required to be sterilized after each procedure, which can be costly.

BRIEF SUMMARY OF THE INVENTION

In accordance with one or more embodiments, an inter-locking gear system for robotic catheter navigation systems is provided. Such an inter-locking gear system enables the motors, controller, and other non-disposable parts of the robotic catheter navigation system to be isolated via a sterile bag, thereby reducing the amount of sterilization required after each procedure.

In accordance with one or more embodiments, a robotic catheter navigation system is provided. The robotic catheter navigation system comprises a catheter handle, a motor, and a torque transfer disk. The catheter handle comprises a set of gears coupled to a first shaft. The motor is for rotating a second shaft. The torque transfer disk is coupled to the first shaft and the second shaft for transferring the rotation of the second shaft to the first shaft to thereby rotate the set of gears for steering a catheter.

In one embodiment, the torque transfer disk is an outer torque transfer disk and the catheter handle comprises a second set of gears coupled to a third shaft. In this embodiment, the robotic catheter navigation system further comprises a second motor for rotating a fourth shaft and an inner torque transfer disk configured to nest within the outer torque transfer disk. The inner torque transfer disk is coupled to the third shaft and the fourth shaft for transferring the rotation of the fourth shaft to the third shaft to thereby rotate the second set of gears for steering the catheter. In one embodiment, the outer torque transfer disk comprises a plurality of separable portions for nesting the inner torque transfer disk within the outer torque transfer disk. In one embodiment, the third shaft is configured to nest within the first shaft such that the third shaft and the first shaft are independently rotatable and the fourth shaft is configured to nest within the second shaft such that the fourth shaft and the second shaft are independently rotatable.

In one embodiment, the torque transfer disk comprises a first surface including an interface for coupling to the first shaft and a second surface including an interface for coupling to the second shaft.

In one embodiment, the robotic catheter navigation system comprises an interface plate comprising a top plate and a bottom plate. The top plate is configured to couple to the bottom plate for mounting the torque transfer disk therebetween.

In one embodiment, the catheter handle comprises a hatch configured to expose the set of gears for manually rotating the set of gears. In another embodiment, the catheter handle comprises one or more buttons for manually rotating the set of gears.

In accordance with one or more embodiments, a torque transfer disk is provided having a first interface and a second interface. The first interface is for coupling to a first shaft, which is coupled to a set of gears in a catheter handle. The second interface is for coupling to a second shaft. The torque transfer disk is configured to transfer rotation of the second shaft to the first shaft to thereby rotate the set of gears for steering a catheter.

In one embodiment, the torque transfer disk is an inner torque transfer disk configured to nest within an outer torque transfer disk. In another embodiment, the torque transfer disk is an outer torque transfer disk configured to nest an inner torque transfer disk. The outer torque transfer disk comprises a plurality of separable portions for nesting the inner torque transfer disk within the outer torque transfer disk.

In one embodiment, the torque transfer disk comprises a first surface including the first interface for coupling to the first shaft and a second surface including the second interface for coupling to the second shaft.

In accordance with one or more embodiments, a method for operating a robotic catheter navigation system is provided. The robotic catheter navigation system comprises a catheter handle, which comprises a set of gears coupled to a first shaft. A second shaft is rotated. The rotation of the second shaft is transferred to a first shaft using a torque transfer disk coupled to the first shaft and the second shaft. Rotation of the first shaft thereby rotates the set of gears for steering a catheter.

In one embodiment, the catheter handle further comprises a second set of gears coupled to a third shaft and the torque transfer disk is an outer torque transfer disk. A fourth shaft is rotated. The rotation of the fourth shaft is transferred to the third shaft using an inner torque transfer disk coupled to the third shaft and the fourth shaft. The inner torque transfer disk is configured to nest within the outer torque transfer disk. Rotation of the third shaft thereby rotates the second set of gears for steering the catheter. The outer torque transfer disk comprises a plurality of separable portions for nesting the inner torque transfer disk within the outer torque transfer disk. The third shaft is configured to nest within the first shaft such that the third shaft and the first shaft are independently rotatable and the fourth shaft is configured to nest within the second shaft such that the fourth shaft and the second shaft are independently rotatable.

In one embodiment, the catheter handle comprises a hatch configured to expose the set of gears for manually rotating the set of gears. In another embodiment, the catheter handle comprises one or more buttons for manually rotating the set of gears.

These and other advantages of the invention will be apparent to those of ordinary skill in the art by reference to the following detailed description and the accompanying drawings.

BRIEF DESCRIPTION OF THE DRAWINGS

FIG. 3C shows a bottom perspective view of torque transfer disk in an assembled state, in accordance with one or more embodiments;

DETAILED DESCRIPTION

Figure 1:
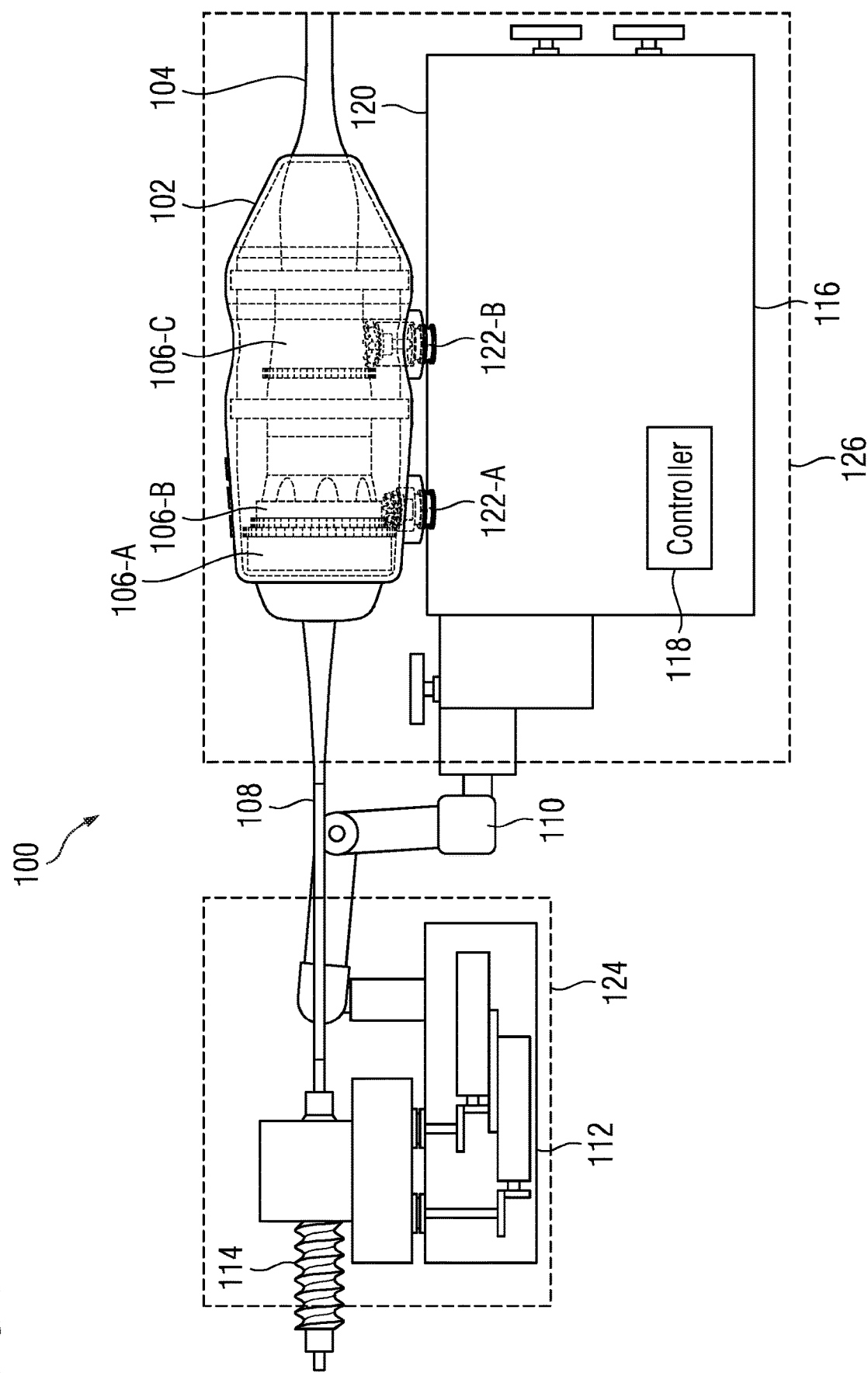
FIG. 1 shows an exemplary robotic catheter navigation system, in accordance with one or more embodiments.

The present invention generally relates to an interlocking gear system for a robotic catheter navigation system, and method for operation thereof. Embodiments of the present invention are described herein to give a visual understanding of such methods and systems. Embodiments of the present invention are described herein with reference to the figures, where like reference numerals represent the same or similar elements.

During an ICE procedure, a catheter is navigated within the heart of a patient. A transducer, mounted at the tip of the catheter, transmits ultrasonic signals and receives reflections of the ultrasonic signals to thereby generate high-resolution images from within the heart. To assist in navigating the catheter, a robotic catheter navigation system may be implemented for assisted steering of the catheter to enable a user (e.g., cardiologist, a clinician, or any other user) to manipulate the catheter in all four degrees of freedom (i.e., anterior/posterior tip bending, left/right tip bending, rotation, and translation) needed to fully steer the catheter. One example of such a robotic catheter navigation system is shown in FIG. 1. Other exemplary robotic catheter navigation systems are described in U.S. patent application Ser. No. 16/809,067, filed Mar. 4, 2020, and U.S. patent application Ser. No. 16/907,675, filed Jun. 22, 2020, the disclosures of which are incorporated herein by reference in their entirety.

FIG. 1 shows an exemplary robotic catheter navigation system 100, in accordance with one or more embodiments. Robotic catheter navigation system 100 comprises a catheter 108, a base 116, a catheter handle 102, an access point base 112, an access point guide 114, and an arm 110. In one embodiment, catheter 108 is an ICE catheter for performing an ICE procedure, but may be any other suitable catheter. Catheter handle 102 is mounted on base 116 via one or more interface plates 120. Base 116 and catheter handle 102 form a handle robot 126. Access point base 112 and access point guide 114 form an access point robot 124. Arm 110 connects or links handle robot 126 to access point robot 124. Cable 104 interfaces with an ultrasound device (not shown) for, e.g., image processing, beam forming, displaying the generated image, etc. It should be understood that robotic catheter navigation system 100 of FIG. 1 is exemplary and other configurations of robotic catheter navigation system 100 are possible.

In operation, a user manipulates (e.g., rotates) one or more rotatable knobs 106-A, 106-B, and 106-C (collectively referred to as knobs 106) to steer catheter 108. One or more steering wires (not shown) within catheter 108 are connected to one or more knobs 106 such that rotation of knobs 106 apply pushing or pulling forces on the steering wires to thereby control the bend at a tip of catheter 108. In one embodiment, knob 106-A is for controlling a bending of the tip of catheter 108 in an anterior/posterior direction, knob 106-B is for controlling a bending of the tip of catheter 108 in a left/right direction, and knob 106-C is for rotating catheter 108 within catheter handle 102. One or more motors in base 116 drive gears in handle robot 126 to actuate movement of catheter 108. Access point robot 124 manipulates catheter 108 to provide more direct control of catheter 108 near the insertion point of the patient. Access point robot 124 is configured to translate catheter 108 along its longitudinal axis and/or rotate catheter 108 about its longitudinal axis. Accordingly, robotic catheter navigation system 100 enables steering of catheter 108 is all four degrees of freedom—anterior/posterior tip bending, left/right tip bending, rotation, and translation.

In one embodiment, a controller 118 may be implemented in base 116. Controller 118 may comprise a memory and a processor for executing computer program instructions (i.e., code) stored in the memory for robotic steering of catheter 108. Controller 118 may be implemented in any other suitable form, such as, e.g., an application specific integrated circuit, integrated circuit, digital signal processor, field programmable gate array, or any other suitable control device for controlling the motors of the robotic catheter navigation system 100.

Figure 2:
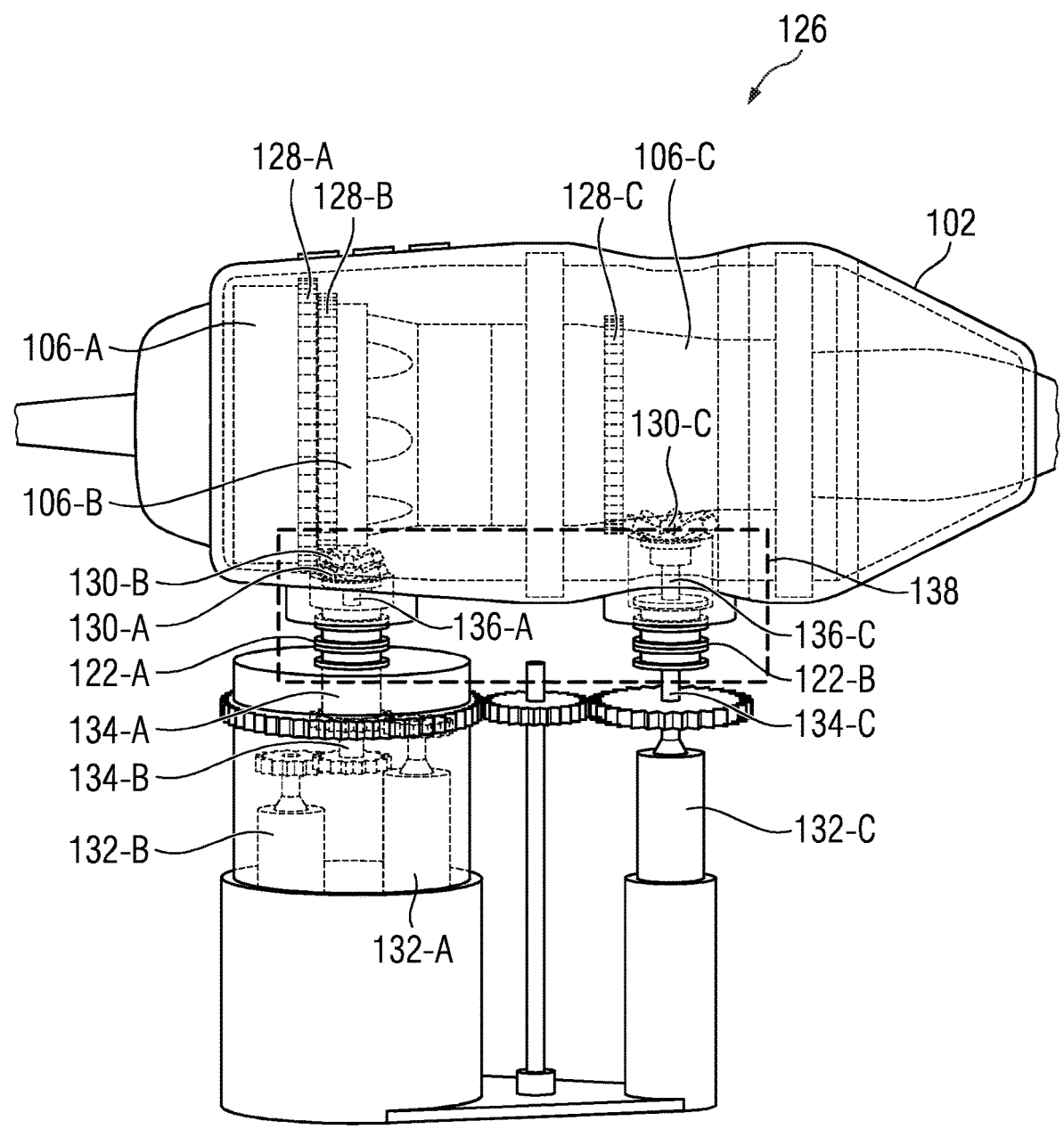
FIG. 2 shows further details of a robot handle of a robotic catheter navigation system, in accordance with one or more embodiments.

FIG. 2 shows further details of a robot handle 126 of robotic catheter navigation system 100, in accordance with one or more embodiments. As shown in FIG. 2, catheter handle 102 comprises gears 128-A, 128-B, and 128-C (collectively referred to as gears 128) which respectively couple to knobs 106-A, 106-B, and 106-C. Catheter handle 102 also comprises gears 130-A, 130-B, and 130-C (collectively referred to as gears 130) for mating with and rotating gears 128-A, 128-B, and 128-C respectively. In one embodiment, gears 128 and 130 are circular bevel gears, but may alternatively be flat or straight gears, gears with tracks on the side of a disc shape, or any other suitable gear. Gears 128 and 130 form sets of gears in catheter handle 102 for robotically steering catheter 108. A first set of gears comprises gears 128-A and 130-A, which are mated together for controlling knob 106-A for steering catheter 108 in an anterior/posterior direction. A second set of gears comprises gears 128-B and 130-B, which are mated together for controlling knob 106-B for steering catheter 108 in a left/right direction. A third set of gears comprises gears 128-C and 130-C, which are mated together for controlling knob 106-C for rotating catheter 108 about a longitudinal axis of catheter handle 102.

Motors 132-A, 132-B, and 132-C (collectively referred to as motors 132) drive gears 128 and 130 for robotically steering catheter 108. Motors 132 may be enclosed within base 116 of robot handle 126. In one embodiment, motors 132 are, e.g., servo motors, rotational motors, linear motors (e.g., linear magnetic motors), but may be any other electric, pneumatic, or hydraulic motors or any other suitable motors. Motors 132 rotate shafts 134-A, 134-B, and 134-C (collectively referred to as shafts 134) for driving gears 128 and 130 via torque transfer disks 122. Torque transfer disks are mounted and secured within interface plate 120 (not shown in FIG. 2 for clarity). An exploded view of portion 138 is shown in in FIG. 5.

It should be understood that FIG. 2 shows additional features of catheter handle 126 that are not important for the understanding of the present invention and will therefore not be discussed in detail.

Figure 3A:
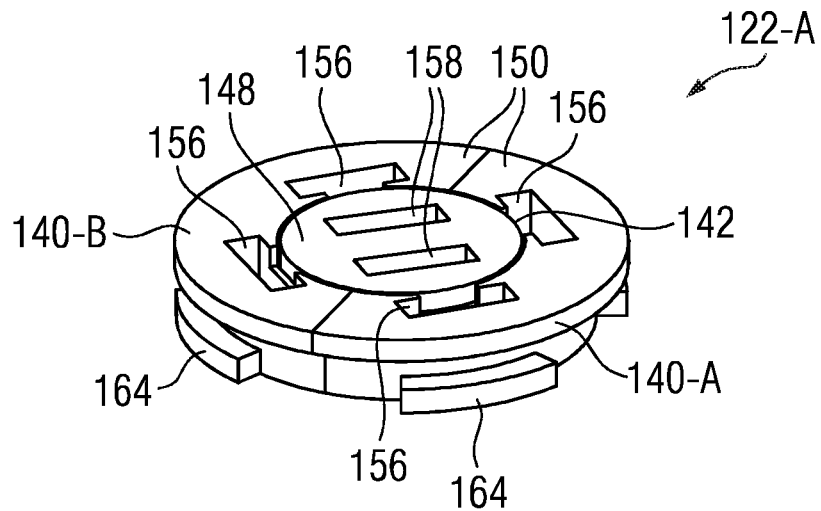
FIG. 3A shows a top perspective view of torque transfer disk in an assembled state, in accordance with one or more embodiments.
Figure 3B:
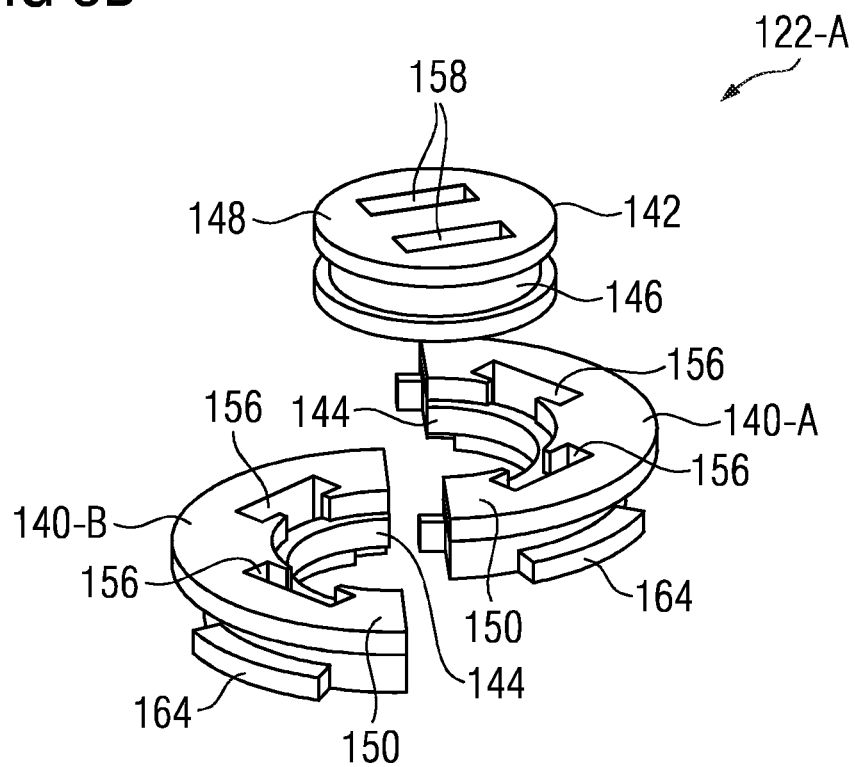
FIG. 3B shows a top perspective view of torque transfer disk in an unassembled state, in accordance with one or more embodiments.

Referring to FIGS. 3A-3C, further details of torque transfer disk 122-A are shown, in accordance with one or more embodiments. FIG. 3A shows a top perspective view of torque transfer disk 122-A in an assembled state. FIG. 3B shows a top perspective view of torque transfer disk 122-A in an unassembled state. FIG. 3C shows a bottom perspective view of torque transfer disk 122-A in an assembled state.

As shown in FIGS. 3A-3C, torque transfer disk 122-A comprises an inner disk 142 and an outer disk 140. Outer disk 140 comprises a first portion 140-A and a second portion 140-B (collectively forming outer disk 140), which are configured to separate to allow inner disk 142 to be nested within outer disk 140. Once assembled, outer disk 140 is ring shaped with a hollow center. As shown in FIG. 3B, outer disk 140 comprises an inner edge comprising a protruding edge portion 144 and inner disk 142 comprises an outer edge comprising a recessed edge portion 146. Inner disk 142 is configured to nest within outer disk 140 such that protruding edge portion 144 of outer disk 140 is positioned within recessed edge portion 146 of inner disk 146, thereby allowing outer disk 140 and inner disk 142 to rotate independently.

Outer disk 140 comprises a first (e.g. top) surface 150 (FIGS. 3A-3B) having one or more female interfaces 156 and a second (e.g., bottom) surface 154 (FIG. 3C) having one or more female interfaces 160. Inner disk 142 comprises a first surface 148 (FIGS. 3A-3B) having one or more female interfaces 158 and a second surface 152 (FIG. 3C) having one or more female interfaces 162. Female interfaces 160 and 162 are configured for interfacing with (e.g., coupling or mating with) shafts 134-A and 134-B associated with motors 132-A and 132-B to thereby couple outer disk 140 and inner disk 142 with shafts 134-A and 134-B respectively. Female interfaces 156 and 158 are configured for interfacing with shafts 136-A and 136-B (shown in FIG. 5) to thereby couple outer disk 140 and inner disk 142 with shafts 134-A and 134-B respectively for driving gears 130-A and 130-B. Outer disk 140 and inner disk 142 thereby transfer rotation from shafts 134-A and 134-B to shafts 136-A and 136-B respectively. Torque transfer disk 122-A is mounted within interface plates 120 and secured by flanges 164 on outer disk 140.

Figure 4A:
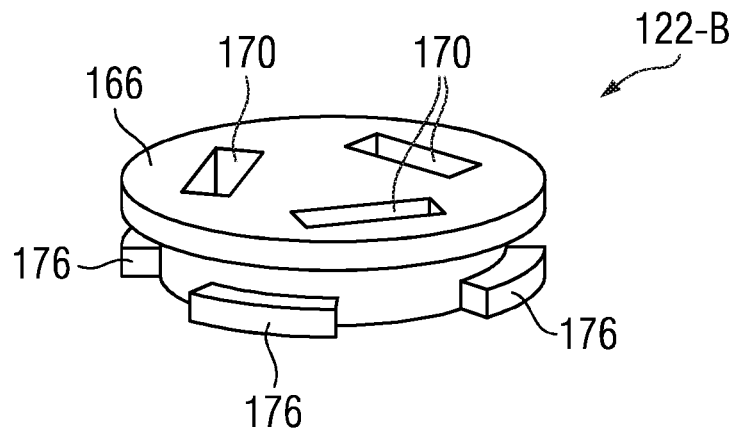
FIG. 4A shows a top perspective view of torque transfer disk, in accordance with one or more embodiments.
Figure 4B:
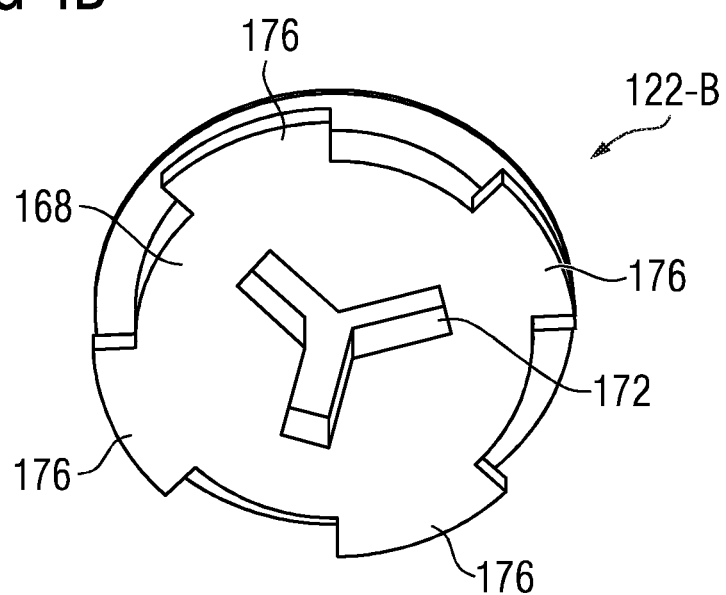
FIG. 4B shows a bottom perspective view of torque transfer disk, in accordance with one or more embodiments.

Referring to FIGS. 4A-4B, further details of torque transfer disk 122-B are shown, in accordance with one or more embodiments. FIG. 4A shows a top perspective view of torque transfer disk 122-B. FIG. 4B shows a bottom perspective view of torque transfer disk 122-B. Torque transfer disk 122-B comprises a first surface 166 having one or more female interfaces 170 and a second surface 168 having one or more female interfaces 172. Female interfaces 172 are configured for interfacing with shaft 134-C associated with motor 132-C to thereby couple torque transfer disk 122-B with shaft 134-C. Female interfaces 170 are configured for interfacing with shaft 136-C to thereby couple torque transfer disk 122-B with shaft 134-C for driving gear 130-C. Torque transfer disk 122-B thereby transfers torque from shaft 134-C to shaft 136-C. Torque transfer disk 122-B is mounted within interface plates 120 and secured by flanges 176.

Figure 5:
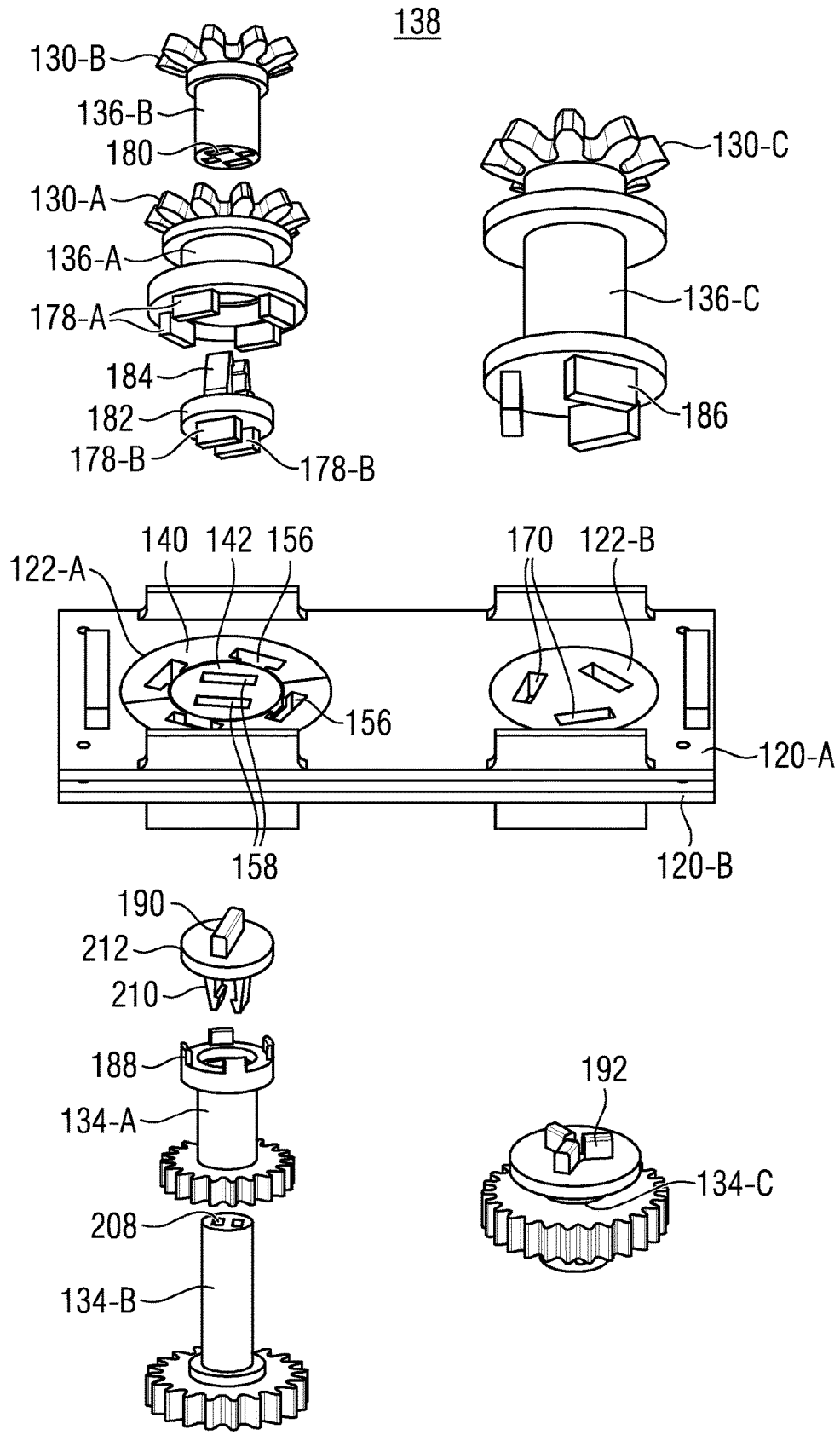
FIG. 5 shows an exploded view of portion 138 of FIG. 2, in accordance with one or more embodiments.

FIG. 5 shows an exploded view of portion 138 of FIG. 2, in accordance with one or more embodiments. FIG. 5 will be described with continued reference to FIG. 2. Torque transfer disks 122 are mounted between a top plate 120-A and a bottom plate 120-B of interface plate 120 for transferring torque to gears 130 from motors 132 (not shown in FIG. 5).

Shaft 134-A comprises one or more male interfaces 188 for interfacing with female interfaces 160 on second surface 154 (not shown in FIG. 5) of outer disk 140 of torque transfer disk 122-A. Shaft 134-A is rotated by motor 132-A. Shaft 134-B is configured to be nested within shaft 134-A and is rotated by motor 132-B. Once nested, shaft 134-B may be implemented with female-to-male adapter 212 having one or more male interfaces 210 for interfacing with female interface 208 of shaft 134-B and one or more male interfaces 190 for interfacing with one or more female interfaces 162 on second surface 152 (not shown in FIG. 5) of inner disk 142. Shafts 134-A and 134-B are independently rotatable.

Shaft 136-A comprises one or more male interfaces 178-A at a first end and gear 130-A at a second end. Male interfaces 178-A are configured to interface with female interfaces 156 on first surface 150 of outer disk 140. Shaft 136-B comprises one or more female interfaces 180 at a first end and gear 130-B at a second end. Shaft 136-B is configured to be nested within shaft 136-A. Once nested, shaft 136-B may be implemented with a female-to-male adapter 182 having one or more male interfaces 184 for interfacing with female interfaces 180 of shaft 136-B and one or more male interfaces 178-B for interfacing with female interfaces 158 on first surface 148 of inner disk 142. Shafts 136-A and 136-B are independently rotatable.

Shaft 134-C comprises one or more male interfaces 192 for interfacing with female interfaces 172 on second surface 168 (not shown in FIG. 5) of torque transfer disk 122-B. Shaft 134-C is rotated by motor 132-C. Shaft 136-C comprises one or more male interfaces 186 at a first end and gears 130-C at a second end. Male interfaces 186 are configured to interface with female interfaces 170 on first surface 166 of torque transfer disk 122-B.

Figure 6A:
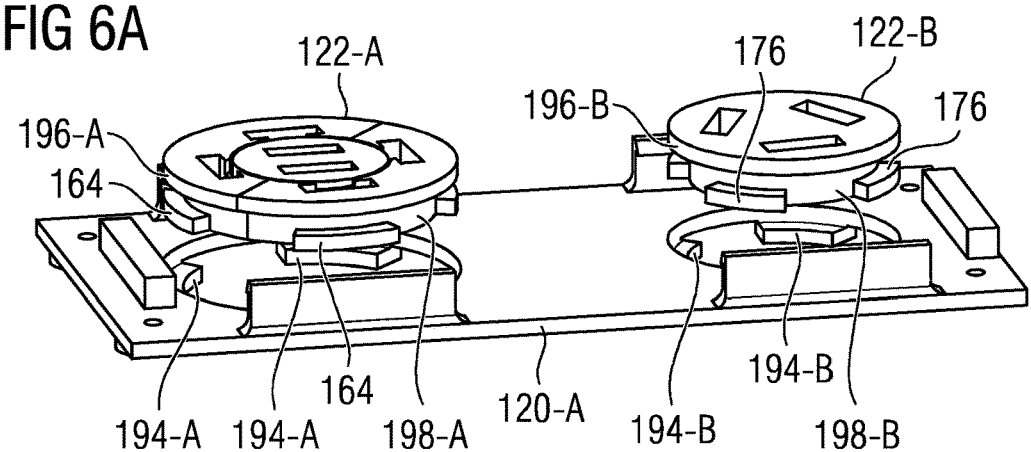
FIG. 6A shows torque transfer disks being mounted in a top plate, in accordance with one or more embodiments.

Referring to FIG. 6A-6E, torque transfer disks 122 are shown being mounted and secured within interface plate 120, in accordance with one or more embodiments. As shown in FIG. 6A, torque transfer disks 122-A and 122-B are mounted in top plate 120-A by rotating torque transfer disks 122-A and 122-B such that flanges 164 and 176 are positioned between protrusions 194-A and 194-B of top plate 120-A, respectively. Projecting edges 196-A and 196-B of torque transfer disks 122-A and 122-B are thereby positioned atop protrusions 194-A and 194-B while flanges 164 and 176 are positioned below protrusions 194-A and 194-B.

Figure 6B:
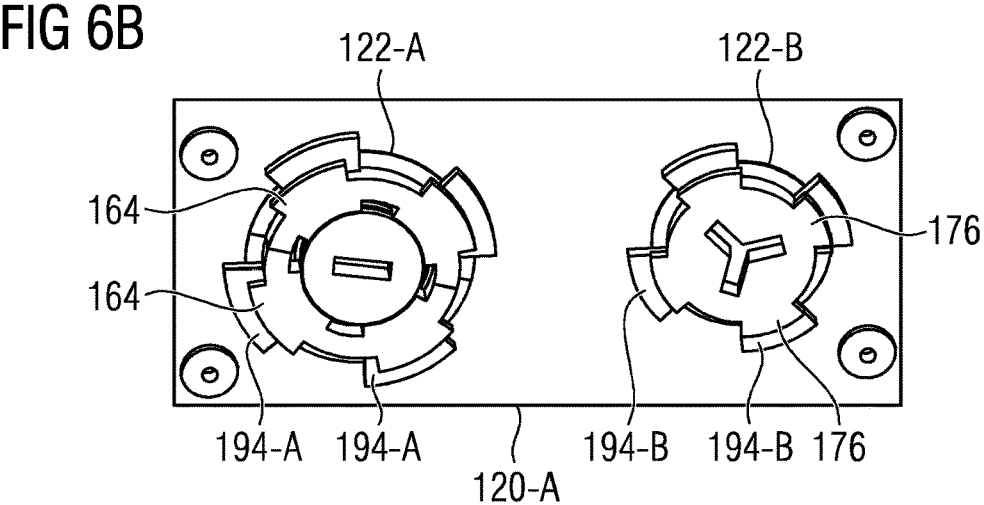
FIG. 6B shows a bottom view of torque transfer disks being mounted within a top plate, in accordance with one or more embodiments.

FIG. 6B shows a bottom view of torque transfer disks 122 mounted within top plate 120-A. Once positioned in top plate 120-A, torque transfer disks 122-A and 122-B are then rotated such that flanges 164 and 176 align with protrusions 194-A and 194-B, respectively. This allows top plate 120-A to couple with bottom plate 120-B.

Figure 6C:
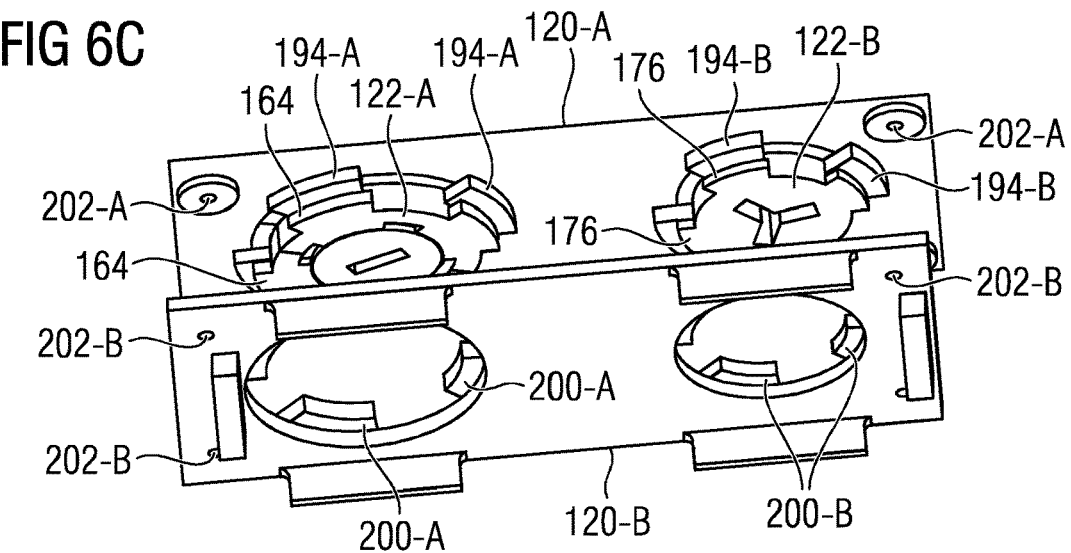
FIG. 6C shows a top plate coupling with a bottom plate to mount torque transfer disks within an interface plate, in accordance with one or more embodiments.

FIG. 6C shows top plate 120-A coupling with bottom plate 120-B to mount torque transfer disks 122 within interface plate 120. Bottom plate 120-B comprises protrusions 200-A and 200-B. In one embodiment, protrusions 200-A and 200-B of bottom plate 120-B are inversely positioned with respect to protrusions 194-A and 194-B of top plate 120-A such that protrusions 200-A and 200-B and protrusions 194-A and 194-B respectively form complete rings when bottom plate 120-B is coupled with top plate 120-A. As shown in FIG. 6C, flanges 164 and 176 are aligned with protrusions 194-A and 194-B to allow protrusions 200-A and 200-B to be positioned therebetween, thereby allowing bottom plate 120-B to couple with top plate 120-A.

Once coupled, top plate 120-A and bottom plate 120-B may be secured together via one or more screws in holes 202-A on top plate 120-A and holes 202-B on bottom plate 202-B. Other attachment mechanisms are also contemplated.

In one embodiment, a sterile bag is positioned between top plate 120-A and bottom plate 120-B to isolate base 116 (including motors 132, controller 118, etc.) from blood or other contaminants encountered during a procedure. The sterile bag may have holes where torque transfer disks 122 are positioned and possible holes where holes 202-A and 202-B are positioned.

Figure 6D:
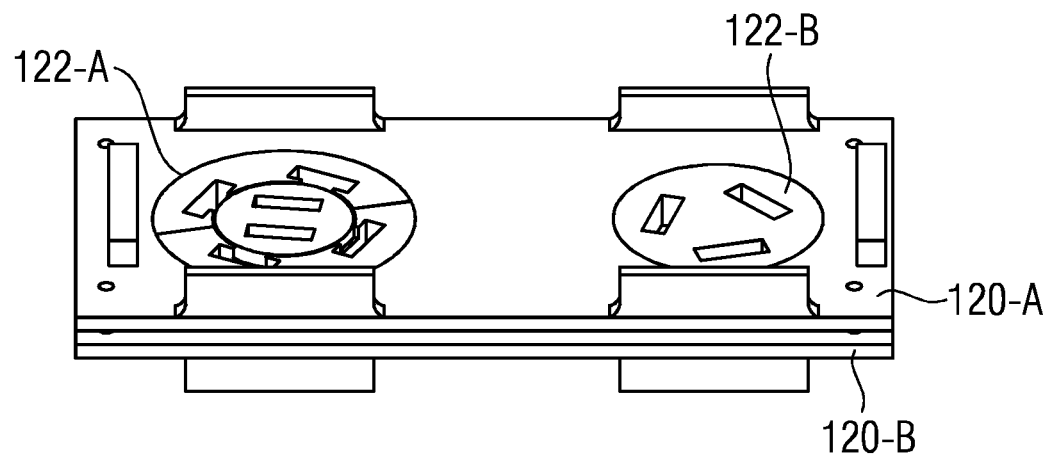
FIG. 6D shows a top perspective view of a top plate coupled with a bottom plate with torque transfer disks mounted therebetween, in accordance with one or more embodiments.
Figure 6E:
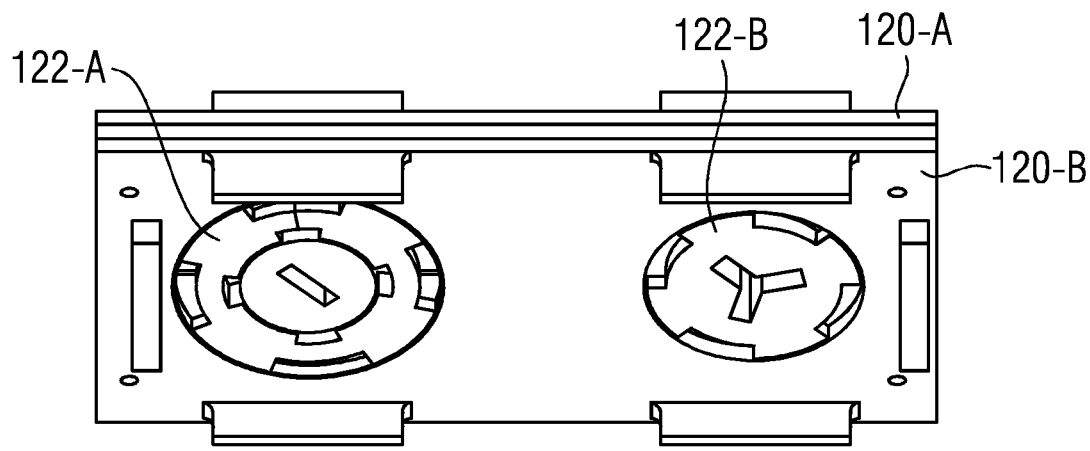
FIG. 6E shows a bottom perspective view of a top plate coupled with a bottom plate with torque transfer disks mounted therebetween, in accordance with one or more embodiments.

FIG. 6D shows a top perspective view of top plate 120-A coupled with bottom plate 120-B with torque transfer disks 122 mounted therebetween. FIG. 6E shows a bottom perspective view of top plate 120-A coupled with bottom plate 120-B with torque transfer disks 122 mounted therebetween. Once bottom plate 120-B and top plate 120-A are coupled, projecting edges 196-A and 196-B of torque transfer disks 122-A and 122-B are positioned atop protrusions 194-A and 194-B and protrusions 200-A and 200-B to thereby support torque transfer disks 122-A and 122-B respectively. Protrusions 194-A and 194-B and protrusions 200-A and 200-B are positioned within channels 198-A and 198-B (FIG. 6A) formed between projecting edges 196-A and 196-B and protrusions 194 and 196 respectively allowing torque transfer disks 122-A and 122-B to freely rotate.

Figure 7:
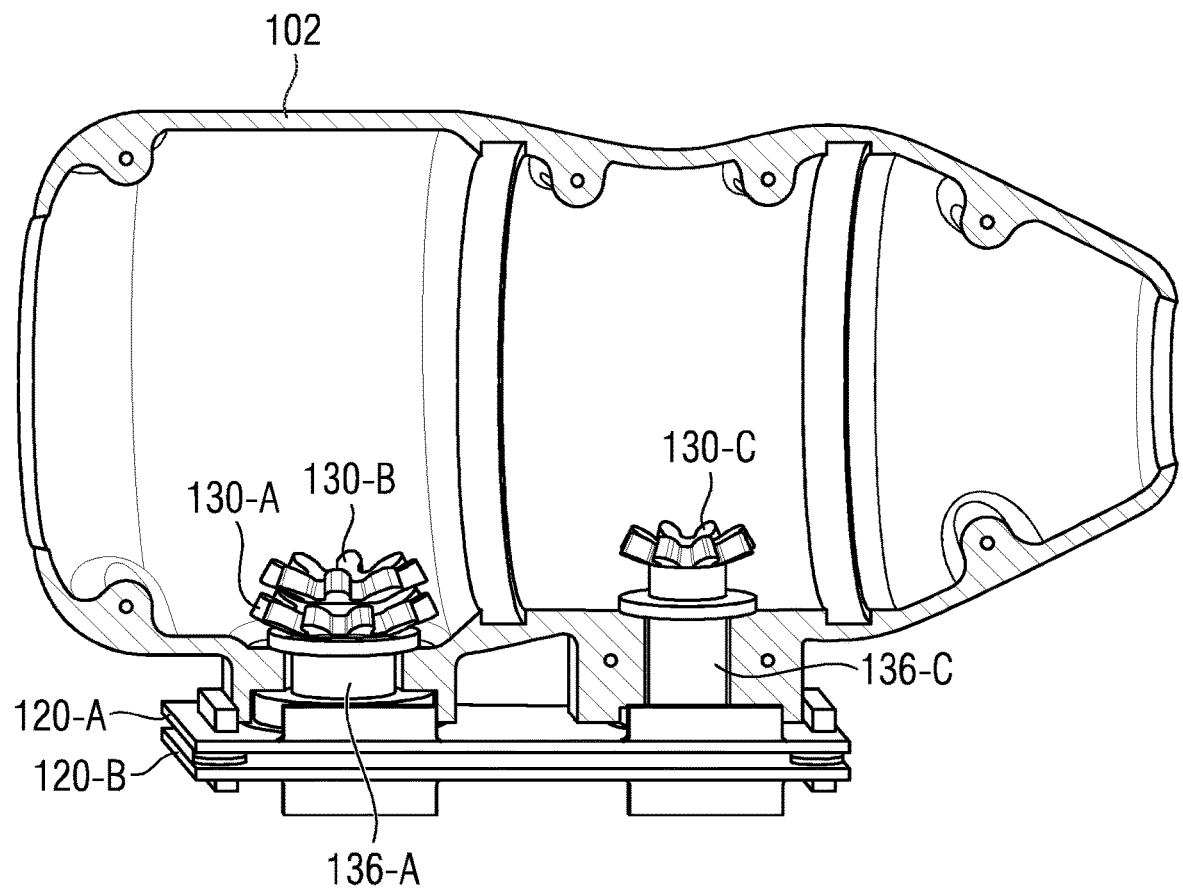
FIG. 7 shows a cross-sectional view of a catheter handle, in accordance with one or more embodiments.

FIG. 7 shows a cross-sectional view of catheter handle 102, in accordance with one or more embodiments. Catheter handle 102 is mounted on top plate 120-A to receive gears 130 for robotically steering catheter 108. Gears 130 are flanged to maintain their position in applications where the lengths of shafts 136 are short.

In one embodiment, robotic catheter navigation system 100 may be configured to provide a fallback system for manual control. Such manual control may be beneficial where robotic catheter navigation system 100 malfunctions (e.g., due to a power failure) or the user otherwise prefers to manually control steering of catheter 108. Accordingly, robotic catheter navigation system 100 may be configured for both automatic robotic steering and manual steering by a user.

Figure 8:
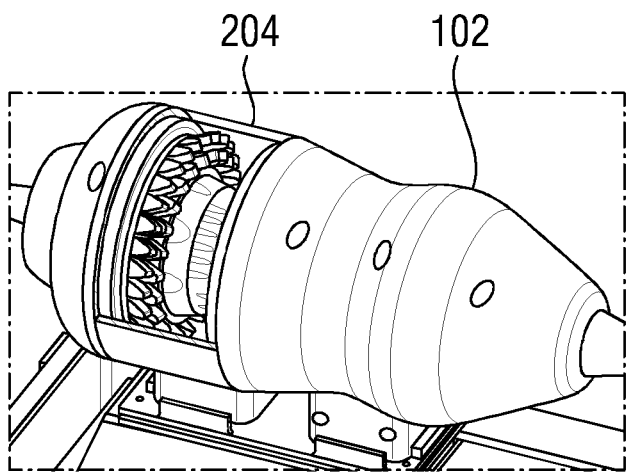
FIG. 8 shows a catheter handle having a hatch for enabling a user to manually steer a catheter, in accordance with one or more embodiments.

FIG. 8 shows catheter handle 102 having a hatch 204 for enabling a user to manually steer catheter 108, in accordance with one or more embodiments. Hatch 204 may be opened or otherwise removed to enable user access to gears 128. A user may thereby manually rotate gears 128 in catheter handle 102 for manually steering catheter 108. In one embodiment, hatch 204 is translucent but may be of any suitable material.

Figure 9:
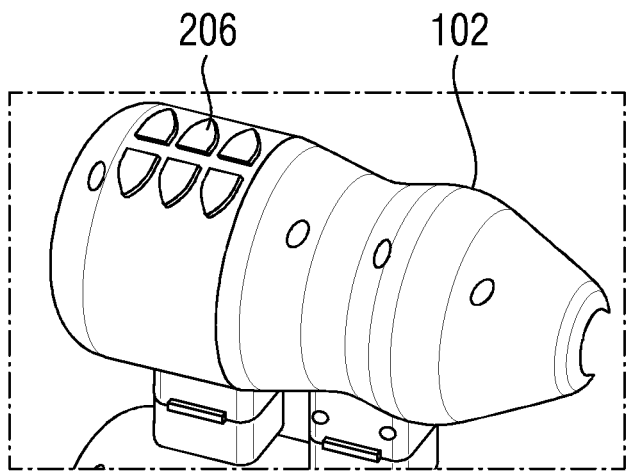
FIG. 9 shows a catheter handle having one or more buttons for enabling a user to manually steer a catheter, in accordance with one or more embodiments.

FIG. 9 shows catheter handle 102 having one or more buttons 206 for enabling a user to manually steer catheter 108, in accordance with one or more embodiments. Buttons 206 mechanically rotate gears 128 in catheter handle 102. In one embodiment, buttons 206 comprises a first button and a second button for respectively rotating gear 128-A in a clockwise and a counter clockwise direction for steering catheter 108 in an anterior/posterior direction, a third button and a fourth button for respectively rotating gear 128-B in a clockwise and a counter clockwise direction for steering catheter 108 in a left/right direction, and a fifth button and a sixth button for respectively rotating gear 128-C in a clockwise and a counter clockwise direction for rotating catheter 108 about a longitudinal axis of catheter handle 102. Buttons 206 enable manual control of catheter 108 when allowing catheter handle 102 to remain closed during a procedure.

Figure 10:
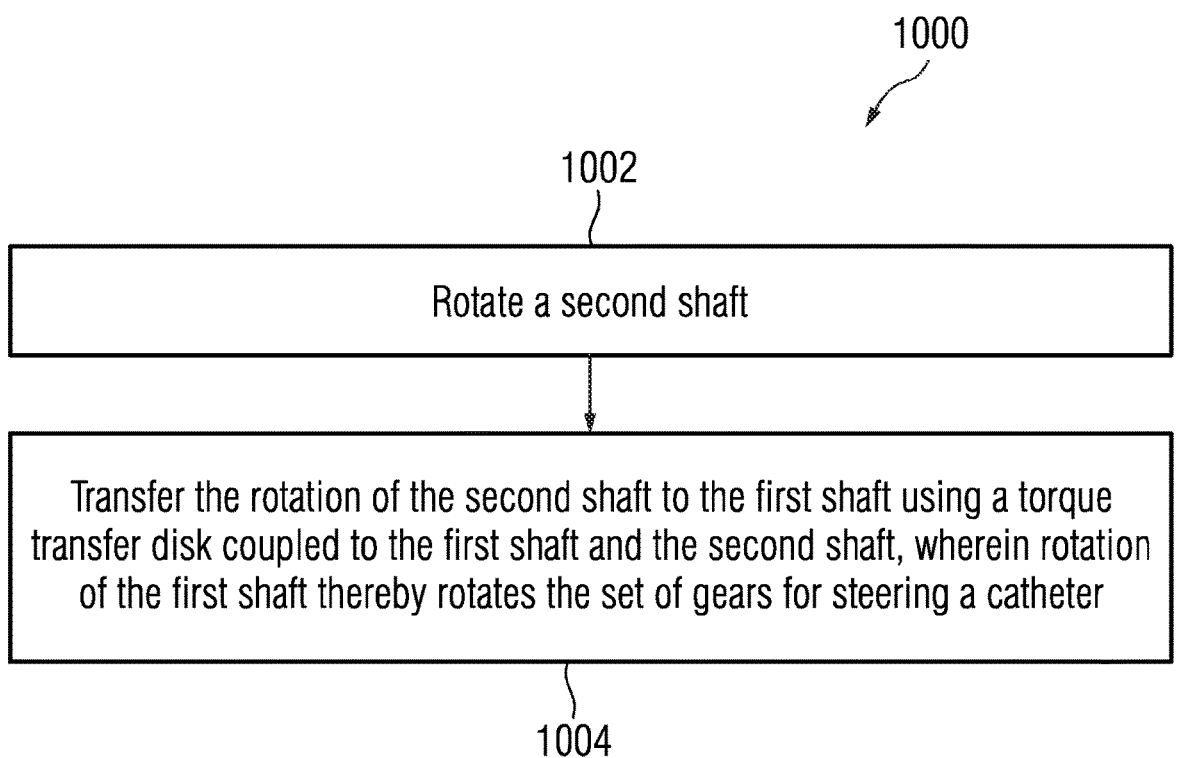
FIG. 10 shows a method for operating a robotic catheter navigation system, in accordance with one or more embodiments.

FIG. 10 shows a method 1000 for operating a robotic catheter navigation system, in accordance with one or more embodiments. The robotic catheter navigation system comprises a catheter handle 102, which comprises a set of gears coupled a first shaft. Method 1000 will be described with continued reference to FIGS. 1-9.

At step 1002, a second shaft is rotated. In one example, the second shaft may be shafts 134-A, 134-B, or 134-C and may be rotated by motors 132-A, 132-B, or 132-C, respectively.

At step 1004, the rotation of the second shaft is transferred to the first shaft using a torque transfer disk coupled to the first shaft and the second shaft. Rotation of the first shaft thereby rotates the set of gears for steering a catheter. In one example, where the second shaft is shaft 134-A, the first shaft is shaft 136-A and the set of gears comprises gears 130-A; where the second shaft is shaft 134-B, the first shaft is shaft 136-B and the set of gears comprises gears 130-B; and where the second shaft is shaft 134-C, the first shaft is shaft 136-C and the set of gears comprises gears 130-C. The torque transfer disk may be outer disk 150 of torque transfer disk 122-A, inner disk 148 of torque transfer disk 122-A, or torque transfer disk 122-B.

In one embodiment, the catheter handle 102 comprises a second set of gears coupled to a third shaft and the torque transfer disk is an outer torque transfer disk (e.g., outer disk 150). A fourth shaft is rotated and the rotation of the fourth shaft is transferred to the third shaft using an inner torque transfer disk (e.g., inner disk 148) coupled to the third shaft and the fourth shaft. The inner torque transfer disk is configured to nest within the outer torque transfer disk. The rotation of the third shaft thereby rotates the second set of gears for steering the catheter. In this embodiment, for example, the first shaft may be shaft 136-A, the second shaft may be shaft 134-A, the third shaft may be shaft 136-B, and the fourth shaft may be shaft 134-B. The third shaft is configured to nest within the first shaft such that the third shaft and the first shaft are independently rotatable and the fourth shaft is configured to nest within the second shaft such that the fourth shaft and the second shaft are independently rotatable.

In one embodiment, the catheter handle comprises a hatch configured to expose the set of gears for manually rotating the set of gears. In another embodiment, the catheter handle comprises one or more buttons for manually rotating the set of gears.

Embodiments described herein provide for torque transfer disks 122 for transferring torque from one or more motors 132 in base 116 to one or more gears 130 in catheter handle 102. Instead of motors 132 directly interacting with gears 130 as in conventional robotic catheter navigation systems, motors 132 and gears 130 indirectly interact via torque transfer disks 122. Advantageously, torque transfer disks 122 enable base 116 (including motors 132) to be isolated from the remainder of robotic catheter navigation system 100 via a sterile bag, thereby minimizing the sanitization required after each procedure.

It should be understood that while certain embodiments described herein are described as being female interfaces (e.g., female interfaces 156, 158, 160, and 162 in FIGS. 3A-3C, female interfaces 170 and 172 in FIGS. 4A-4B, and female interfaces 180 and 208 in FIG. 5) and male interfaces (e.g., male interfaces 178-A, 178-B, 186, 188, 190, and 192 in FIG. 5), the present invention is not so limited. Such female interfaces may be male interfaces and vice versa. Further, such female and male interfaces may be any suitable interface for coupling various elements together and are not limited to male/female interfaces. Such female and male interfaces may be implemented in any suitable configuration (e.g., layout, shape, etc.) and is not limited to the configuration shown in the figures (e.g., FIGS. 3A-3C, 4A-4B, and 5) 5).

While the present invention is described with respect to various embodiments, it should be understood that features and advantages described with respect to one embodiment may apply equally to other embodiments. Embodiments described herein are described with respect to the claimed systems as well as with respect to the claimed methods. Features, advantages or alternative embodiments herein can be assigned to the other claimed objects and vice versa. In other words, claims for the systems can be improved with features described or claimed in the context of the methods. In this case, the functional features of the method are embodied by objective units of the providing system.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A robotic catheter navigation system having a first shaft, a second shaft, a third shaft, and a fourth shaft, the robotic catheter navigation system comprising:
   a catheter handle comprising 1) a first set of gears coupled to the first shaft and 2) a second set of gears coupled to the third shaft;
   a first motor for rotating the second shaft;
   a second motor for rotating the fourth shaft;
   an outer torque transfer disk directly coupled to the first shaft and the second shaft for transferring the rotation of the second shaft to the first shaft to thereby rotate the first set of gears for steering a catheter; and
   an inner torque transfer disk configured to nest within the outer torque transfer disk, the inner torque transfer disk coupled to the third shaft and the fourth shaft for transferring the rotation of the fourth shaft to the third shaft to thereby rotate the second set of gears for steering the catheter.

2. The robotic catheter navigation system of claim 1, wherein the outer torque transfer disk comprises a plurality of separable portions for nesting the inner torque transfer disk within the outer torque transfer disk.

3. The robotic catheter navigation system of claim 1, wherein the third shaft is configured to nest within the first shaft such that the third shaft and the first shaft are independently rotatable.

4. The robotic catheter navigation system of claim 1, wherein the fourth shaft is configured to nest within the second shaft such that the fourth shaft and the second shaft are independently rotatable.

5. The robotic catheter navigation system of claim 1, wherein the outer torque transfer disk comprises a first surface including an interface for coupling to the first shaft and a second surface including an interface for coupling to the second shaft.

6. The robotic catheter navigation system of claim 1, further comprising:
   an interface plate comprising a top plate and a bottom plate, the top plate configured to couple to the bottom plate for mounting the outer torque transfer disk and the inner torque transfer disk therebetween.

7. The robotic catheter navigation system of claim 1, wherein the catheter handle comprises a hatch configured to expose the first set of gears and the second set of gears for manually rotating the first set of gears and the second set of gears.

8. The robotic catheter navigation system of claim 1, wherein the catheter handle comprises one or more buttons for manually rotating the first set of gears and the second set of gears.

9. A method for operating a robotic catheter navigation system having a first shaft, a second shaft, a third shaft, and a fourth shaft, the robotic catheter navigation system comprising a catheter handle, the catheter handle comprising 1) a first set of gears coupled to the first shaft and 2) a second set of gears coupled to the third shaft, the method comprising:
   rotating the second shaft by a first motor;
   rotating the fourth shaft by a second motor;

transferring the rotation of the second shaft to the first shaft using an outer torque transfer disk directly coupled to the first shaft and the second shaft, wherein the rotation of the first shaft thereby causes rotation of the first set of gears for steering a catheter; and transferring the rotation of the fourth shaft to the third shaft using an inner torque transfer disk coupled to the third shaft and the fourth shaft, the inner torque transfer disk configured to nest within the outer torque transfer disk, wherein the rotation of the third shaft thereby causes rotation of the second set of gears for steering the catheter.

10. The method of claim 9, wherein the outer torque transfer disk comprises a plurality of separable portions for nesting the inner torque transfer disk within the outer torque transfer disk.

11. The method of claim 9, wherein:
the third shaft is configured to nest within the first shaft such that the third shaft and the first shaft are independently rotatable, and
the fourth shaft is configured to nest within the second shaft such that the fourth shaft and the second shaft are independently rotatable.

12. The method of claim 9, wherein the catheter handle comprises a hatch configured to expose the first set of gears and the second set of gears for manually rotating the first set of gears and the second set of gears.

13. The method of claim 9, wherein the catheter handle comprises one or more buttons for manually rotating the first set of gears and the second set of gears.

14. The method of claim 9, wherein the outer torque transfer disk comprises a first surface including an interface for coupling to the first shaft and a second surface including an interface for coupling to the second shaft.

\* \* \* \* \*